United States Patent [19]

Monter et al.

[11] 4,290,872

[45] Sep. 22, 1981

[54] HIGH TEMPERATURE REFERENCE ELECTRODE

[75] Inventors: James V. Monter, Alliance; James P. Sorenson, Louisville; George J. Theus, Canton, all of Ohio

[73] Assignee: The Babcock & Wilcox Company, New Orleans, La.

[21] Appl. No.: 52,888

[22] Filed: Jun. 28, 1979

Related U.S. Application Data

[63] Continuation-in-part of Ser. No. 857,850, Dec. 5, 1977, abandoned.

[51] Int. Cl.³ ............................................ G01N 27/30
[52] U.S. Cl. ............................................... 204/195 F
[58] Field of Search ............ 204/195 F, 195 R, 195 P, 204/1 T, 1 H, 1 Y

[56] References Cited

U.S. PATENT DOCUMENTS

| 1,846,354 | 2/1932 | Parker et al. | 204/195 F |
| 2,886,497 | 5/1959 | Butler | 204/1 T |
| 3,701,632 | 10/1972 | Lovelock | 204/195 P |
| 3,835,013 | 9/1974 | Grubb et al. | 204/195 R |

OTHER PUBLICATIONS

J. V. Dobson et al., J. Chem. Soc., Faraday Trans., 1,68, pp. 749-763, (1972).
J. V. Dobson et al., NACE, preprint No. D-9, Jan. 1973.
Digby D. MacDonald, Corrosion, vol. 34, No. 3, pp. 75-84, (1978).
R. S. Greely et al., "Electromotive Force Studies in Aqueous Sol'ns", vol. 64, p. 652, May 1960.

Primary Examiner—G. L. Kaplan
Attorney, Agent, or Firm—Vytas R. Matas; Joseph M. Maguire

[57] ABSTRACT

A hydrogen reference electrode is disclosed which is applicable to measuring systems for determining the oxygen content in high temperature water in the range of 400° F. to the critical point of water of approximately 713° F. at which it co-exists in the liquid and vapor states and which water is treated to provide a reducing atmosphere. The reference electrode is formed as a closed end tube of palladium-Silver alloy material pressurized with hydrogen gas and enclosed in a perforated sleeve which allows water to be trapped in the space between the alloy tube and the sleeve where the water is saturated with hydrogen permeating through the wall of the alloy tube.

4 Claims, 3 Drawing Figures

HIGH TEMPERATURE REFERENCE ELECTRODE

This is a continuation-in-part, of application Ser. No. 857,850, filed Dec. 5, 1977 and now abandoned.

TECHNICAL FIELD

The present invention relates generally to high temperature reference electrodes utilizing hydrogen and particularly to the use of such electrodes in measuring systems for determining the dissolved oxygen content in high temperature water forming a reducing atmosphere.

BACKGROUND ART

There is presently a great need for high temperature reference electrodes which may be used in measuring systems for determining the percentage of dissolved oxygen in high temperature water in the approximate temperature range of 450° F. to 600° F.

Boilermakers, among others, require an accurate measurement of the amount of oxygen or the oxidizing power of the solution in contact with the various corrodible metals comprising the boiler. As an example, light water reactor systems require extreme safety measures because of the potentially catastrophic damage that could be caused by the failure of such a nuclear reactor system. One way for failure to occur in such reactor systems is by way of corrosion of the pipes or tubes conducting high temperature water through the reactor system vessel or steam generator. It is known that corrosion occurs when the concentration of dissolved oxygen in the water of a light water reactor system exceeds 0.2 ppm. Since this level is found in normal city water, light water reactor systems use treated water having dissolved oxygen levels not to exceed 0.2 ppm for boiling water reactor systems and not to exceed 20 ppb for steam generators of pressurized water reactor systems. Oxygen contaminated water may accidentally enter one of the reactor systems. Therefore, a dissolved oxygen measuring system is required which can measure the exact amount of dissolved oxygen in the water of the light water reactor system so that the critical oxygen level may be accurately monitored and controlled.

One of the problems of providing such a dissolved oxygen measuring system has been the unavailability of a reference electrode which would function in a reducing atmosphere at the temperatures, approximately 550° F., at which the water is maintained in the secondary side light water reactor systems. High temperature reference electrodes are known utilizing Silver-Silver Chloride alloys. Such high temperature reference electrodes are satisfactory except in situations where a reducing atmosphere is present, such as is found in a pressurized water reactor system or a fossil reactor system. The hydrogen in the water in the presence of a reducing atmosphere causes the Silver-Silver Chloride material to break down at these elevated temperatures and the reference electrode is no longer Silver-Silver Chloride but becomes through chemical reaction a different material. Thus, it may be seen that the known high temperature reference electrodes are capable of operating only in situations where an oxidizing atmosphere is present and become unstable in a high temperature reducing atmosphere being unable to provide reproducible output signals. In a PhD Thesis submitted by J. B. Lee to Ohio State University in 1978 entitled "Electrochemical Approach to the Corrosion Problems of Several Fe-Ni-Cr Alloys in High Temperature-High Pressure Water," he indicates that a Silver-Silver-Chloride reference electrode used in a reducing atmosphere of high temperature (288° C.) provided an unstable output signal after several hours or a day. At 250° C. the reference electrode was unstable after 4 to 5 days and even at 100° C. the electrode became unstable after 10 days.

From the foregoing we can see that what was needed was a high temperature reference electrode which could operate at temperatures of approximately 550° F. in a reducing atmosphere such as is found in attempting to measure the dissolved oxygen content in water on the secondary side of a pressurized water reactor system.

SUMMARY OF THE INVENTION

The present invention provides a high temperature hydrogen reference electrode which is capable of operating in a reducing or oxidizing atmosphere. The electrode is formed from a closed end tube of palladium-Silver alloy pressurized on the inside with pure hydrogen gas. The alloy tube is loosely encased in a lightly perforated sleeve which allows liquid such as water to be trapped between the alloy tube and the sleeve where the water is saturated with hydrogen permeating through the wall of the alloy tube. The present electrode acts as a hydrogen reference electrode and it will not break down in any environment because the reaction providing the referencing is hydrogen to hydrogen ions regardless of the environment.

The present electrode is thus not only capable of measuring the amount of oxygen in a solution when used with a measuring system but may actually be used to measure the oxidizing power of the solution. That is, if there are some other oxidizers such as ferric ions, chromate ions, or other such similar ions the measuring system utilizing the mentioned reference electrode would also respond to that type of environment.

The use of the mentioned reference electrode in an oxygen measuring system would be as follows. The reference electrode as well as a second electrode responding to the solution to be measured would both be immersed in the solution. The two electrodes would then be electrically connected between a measuring instrument such as a high impedance voltmeter or electrometer. Nickel has been found to be a suitable material for the measuring electrode. The Nickel behaves in an oxygen environment as a second order oxygen electrode and its potential rises when it is in a solution that has dissolved oxygen. If the solution does not have oxygen, the potential of the Nickel electrode falls and the difference between the Nickel electrode and the reference electrode comes close to zero.

From the foregoing it may thus be seen that one aspect of the present invention is to provide a high temperature reference electrode.

Another aspect of the present invention is to provide an oxygen measuring system for determining the oxidizing power of high temperature water.

These and other aspects of the invention will be more clearly understood from a review of the following description of the preferred embodiment when considered with the accompanying drawings.

DESCRIPTION OF THE PREFERRED EMBODIMENT

Figure 1:
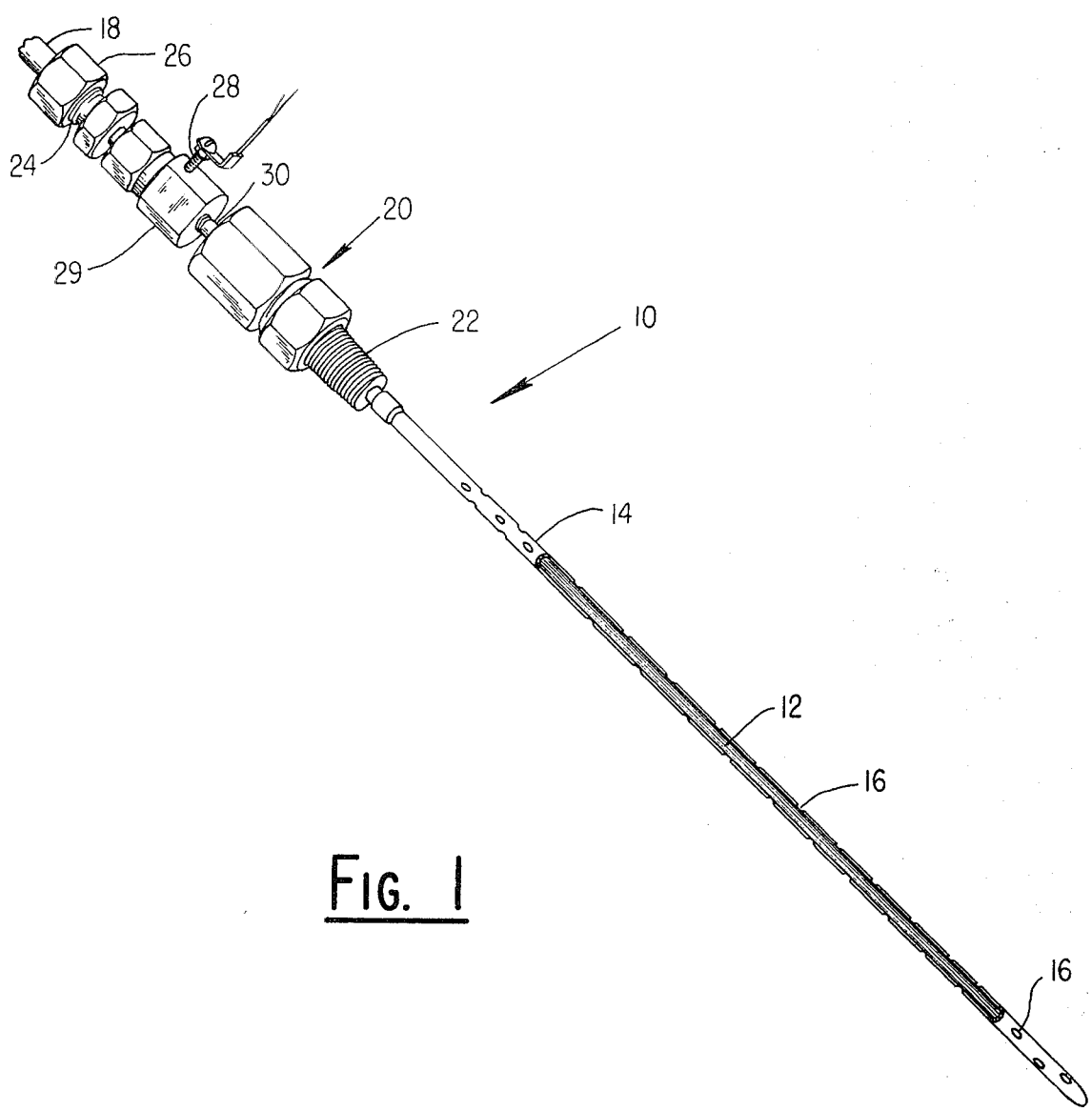
FIG. 1 is a perspective drawing of the high temperature reference electrode of the present invention.

Turning now to the drawings, FIG. 1 teaches a reference electrode assembly 10 having a closed end tube 12 made from a 75% palladium-25% Silver alloy material. This alloy has been found to have significant permeability of hydrogen while remaining very corrosive resistant to high temperature water. The alloy tube 12 is loosely encased in a sleeve 14 having a series of perforations or holes 16 along the entire length of the sleeve 14. The sleeve 14 is made of inert material such as Teflon plastic material and is loosely heat shrunk onto the alloy tube 12 as follows, a length of American Wire Gage (AWG) size 12E tubing sleeve 14 supplied by Penntube Plastic Company (expanded ID 0.150 inch, wall thickness 0.016 inch), 1 inch longer than needed is used to cover the exposed tube 12. The sleeve 14 has a series of holes 16 made in the Teflon tubing starting 1 inch from the end and extending up 5 inches. Between 40 and 60 holes or slits are made using an awl with a shaft diameter of approximately 0.075 inch. The sleeve 14 is slipped over the tube 12 up to the bottom of a Conax fitting 20. A bunsen flame is used to heat the Teflon tubing or sleeve 14 in the area between the bottom of the Conax fitting 20 and down to where the holes 16 start, until the gel temperature is reached (620° F.). This will shrink the tubing tightly onto the tube 12. At the bottom of the tube 12, the 1 inch length of sleeve 14 without holes is also heated to the gel temperature. Approximately ½ inch of the sleeve 14 is shrunk on the end of the tube 12 while the remaining length extending beyond the end of the tube 12 is crimped together using a pair of needlenose pliers until the sleeve 14 cools. This effectively seals the end of the sleeve 14. It should be noted that the area that contains the holes 16 in the sleeve 14 is not heat shrunk. This leaves an annular gap between the outside of the tube 12 and the sleeve 14 of approximately 12.5 mils.

Teflon was chosen because of its ability to be heat shrunk onto the alloy tube 12 as well as its temperature resistance. Teflon will not deteriorate at temperatures below 600° F. Teflon will act as a barrier allowing water to flow only through the holes 16. Various other inert materials would serve just as well for the sleeve 14. In situations where higher temperatures beyond 600° F. were to be encountered (such as up to the critical point of water) or in high velocity flow situations where the Teflon sleeve may be ripped off by the force of the velocity, a metal sleeve of Stainless Steel, Silver, or Nickel may be used. The criteria for the choice of material would be its corrosion resistance, non-pollution of the water stream and nonpermeability to hydrogen. Holes would have to be drilled or punched into the metal sleeve material to allow water to be communicated through the sleeve.

The open end of the alloy tube 12 is connected to a nonelectrical conducting tube 18 which leads to a supply of pressurized hydrogen gas which pressurizes the alloy tube 12 and allows hydrogen to be permeated through the wall of the alloy tube 12.

The alloy tube 12 is mounted to the well known Conax electrical fitting 20 having a threaded portion 22 which may be sealably threaded into a wall of a pressure vessel enclosing pressurized liquid to allow the closed end portion of the alloy tube 12 to be located within the liquid to be sensed. The opposite end of the Conax fitting 20 has a threaded portion 24 through which the hydrogen gas tube 18 is coupled to the open end of the alloy tube 12 by way of a compression nut 26. A setscrew 28 is threaded through an adapter 29 attached to the RULON packing gland of the Conax fitting 20 so as to contact the wall of the alloy tube 12 and to provide an electrical signal pickup therefrom. The setscrew 28 also acts as a coupling maintaining the alloy tube 12 affixed to the Conax fitting 20 thereby preventing the alloy tube 12 from being blown out of the Conax fitting 20 in applications where the alloy tube 12 is sealably mounted in a pressurized vessel.

To prevent the electrical signal tapped from the setscrew 28 from being grounded to the wall of any container into which the Conax fitting 20 will be mounted, an electrically insulating RULON packing gland is mounted between the alloy tube 12 and the Conax fitting 20. The packing gland 30 is a filled material such as film Teflon filled with Alumina Oxides and which is commercially available.

Figure 3:
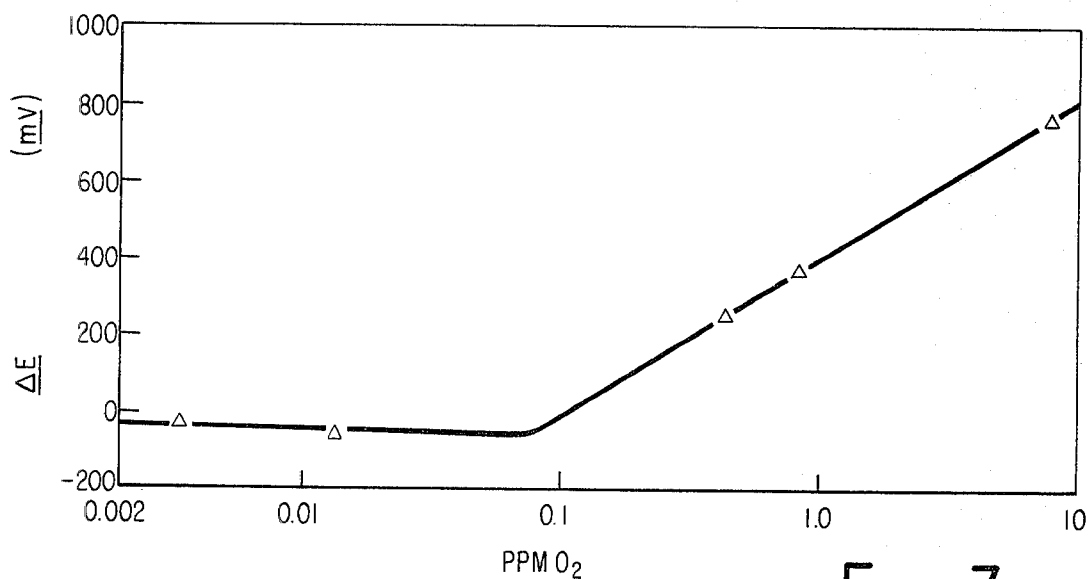
FIG. 3 is a graph of the potential difference exhibited between the reference electrode and the secondary electrode in the measuring system of FIG. 2 when subjected to water having different levels of dissolved oxygen.
Figure 2:
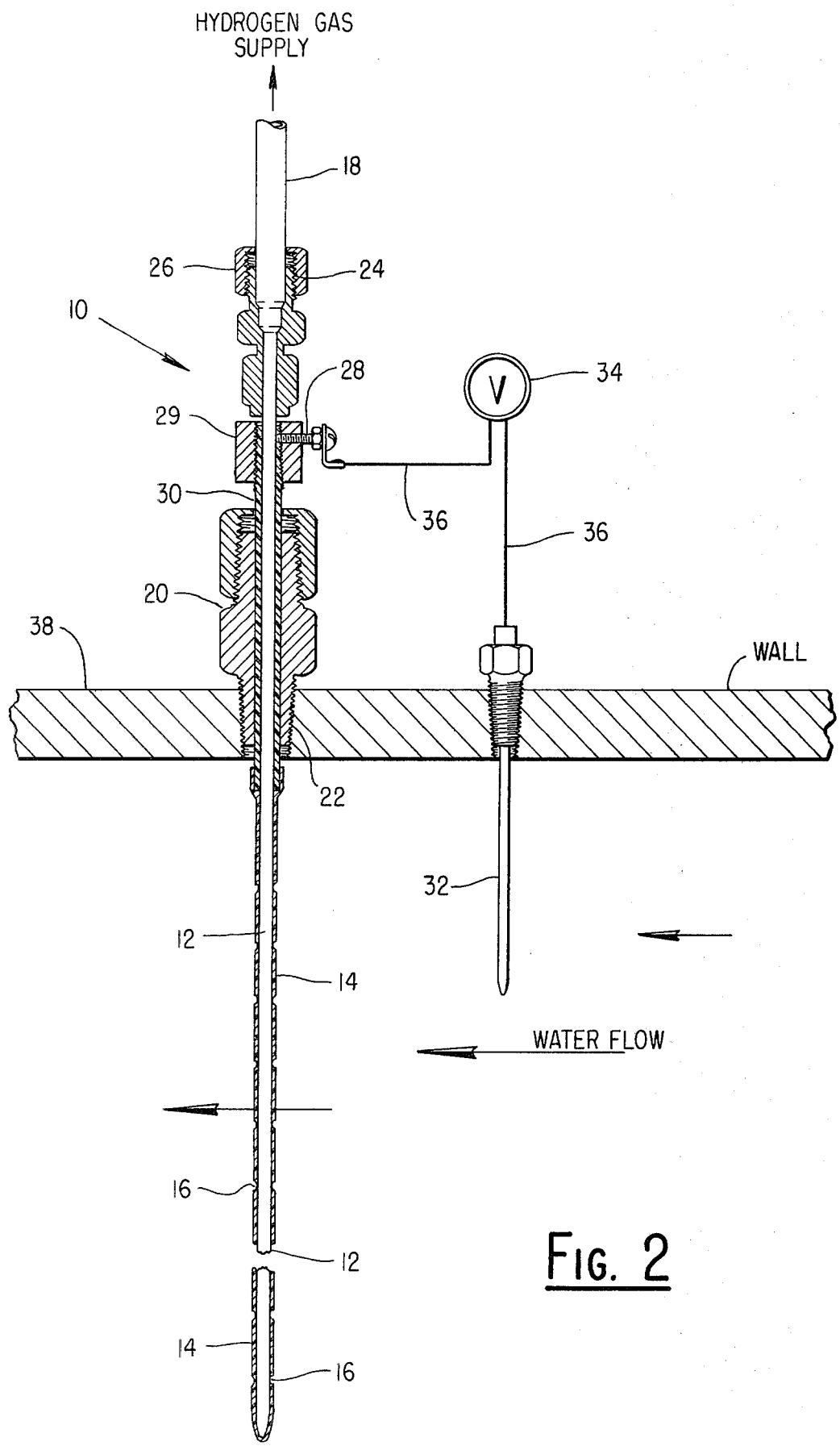
FIG. 2 is a schematic drawing of the reference electrode of FIG. 1 being utilized in an oxygen measuring system for determining the oxidizing power of high temperature water.

Turning now to FIGS. 2 and 3, it will be seen that the reference electrode 10 may be used with a second solid material Nickel-Nickel Oxide electrode 32 to provide a voltage signal in a high impedance voltmeter or electrometer 34 which is electrically connected between the reference electrode 10 and the second electrode 32 by electrical lines 36. The voltage signal established on the high impedance voltmeter of electrometer 34 will be proportional to the amount of dissolved oxygen in the fluid in which both the electrodes are immersed. The two electrodes form half cells in which the potential developed is related by the well-known NERNST equation to the hydrogen ion activity in one cell and the oxygen ion activity in the other cell. As may be seen, both the reference electrode 10 and the second electrode 32 are sealably threaded through a wall 38 on the secondary side of a light water nuclear reactor system so as to be immersed in the flowing water on the secondary side of the reactor system. The water flow is from the Nickel-Nickel Oxide electrode 32 to the reference electrode 10. The electrode 32 is placed upstream of the reference electrode to prevent hydrogen contamination of the actual measuring electrode with reference hydrogen. The distance between the two electrodes is not critical and may be maintained up to a couple electrode lengths. For convenience, the electrodes could be in close proximity to each other.

The water inside of the wall 38 on the secondary side of the light water reactor system will be at a temperature of approximately 400° F. to 550° F. and will be at a pressure of approximately 1200 psi. The water is treated to have a low oxygen content and provides a reducing atmosphere. To maintain the permeability of the hydrogen gas out of the wall of the alloy tube 12, the hydrogen gas supply connected to the alloy tube 12 by the tube 18 is maintained at a pressure higher than the 1200 psi in the secondary side of the reactor system and is held at a 1300 psi pressure level.

As was mentioned earlier, the operation of the cell would be as follows. Water flow inside the wall 38 would allow water to be trapped between the alloy tube 12 and the sleeve 14 by virtue of the holes 16 in the sleeve 14. The water trapped there would be saturated with hydrogen due to the permeability of hydrogen gas through the tube wall 12. As such, the electrode 10 would provide a hydrogen reference where the ion activity is from hydrogen to hydrogen ions and which is a saturated constant forming a half-cell. The oxygen ion activity on the secondary Nickel-Nickel Oxide electrode 32 would then provide a second half-cell potential difference between the reference electrode 10 and the secondary electrode 32 dependent on the amount of dissolved oxygen in the water.

Turning to FIG. 3, it will be seen that the potential difference between these two electrodes in millivolts when immersed in high purity water of approximately 400° F. to 550° F. and at 1200 psi will vary with the oxygen concentration in parts per million as indicated. The high slope linear nature of the curve in the 0.1 ppm to 10 ppm dissolved oxygen level makes this an ideal system for detecting a corrosive water level in the secondary side of the light water reactor system. The slight negative slope of the curve in the 0.01 ppm to 0.1 ppm level also allows measurement of dissolved oxygen concentration in steam generators of pressurized water reactors. The forementioned reference electrode has been in operation in such a described high temperature reducing atmosphere for the last three years and provided a continuously stable output measuring signal and showed no deterioration. Periodically the Teflon sleeve 14 and the gland in the Conax seal were replaced as maintenance procedures.

From the foregoing, it will be seen that the present invention provides a high temperature reference electrode for measuring systems measuring the oxygen content in high temperature, high pressure water forming a reducing atmosphere.

Certain improvements and modifications will occur to those skilled in the art upon reading this specification. Clearly the basic concepts disclosed herein could just as easily be applied to both low temperature measuring systems as well as extremely high temperature measuring systems operating at temperatures in excess of 600° F. and up to the critical point of water. For such extremely high temperature applications different materials would have to be chosen for the sleeve member capable of withstanding the extremely high temperatures. It will be understood that such improvements and modifications were deleted herein for the sake of conciseness and readability but are within the scope of the following claims.

We claim:

1. A reference electrode for detecting dissolved oxygen in a high temperature reducing atmosphere above 400° F. comprising:
    a tube having a closed end and an open end and made of a palladium alloy material predominantly palladium and being permeable to hydrogen;
    a sleeve of material having a series of openings along the length thereof and being affixed around said alloy tube to define a space between said alloy tube and said sleeve; and
    means for connecting the open end of said tube to a supply of hydrogen gas.

2. A reference electrode as set forth in claim 1 wherein said tube is formed from 75% palladium-25% Silver alloy material.

3. A reference electrode as set forth in claim 1 including a hydrogen gas source and wherein said connecting means includes a Conax fitting mounted to said alloy tube and having a compression fitting for connecting a connecting line between said hydrogen gas source and the open end of said alloy tube.

4. A measuring system for determining the amount of dissolved oxygen in a high temperature liquid being above approximately 400° F. and forming a reducing atmosphere comprising:
    a hydrogen reference electrode made of a palladium alloy material permeable to hydrogen gas and providing a stable output signal in said high temperature reducing atmosphere including a tube having a closed end and an open end and made of 75% palladium-25% Silver alloy material permeable to hydrogen, a sleeve of inert material having a series of openings along the length thereof and being affixed around said alloy tube to define a space between said alloy tube and said sleeve and means for connecting the open end of said tube to a supply of hydrogen gas;
    a measuring electrode providing a stable output signal in said high temperature reducing atmosphere;
    electric indicator means connected between said reference electrode and said measuring electrode for indicating the potential difference between said reference electrode and said measuring electrode.

* * * * *